United States Patent
Chiodo et al.

(10) Patent No.: US 7,833,184 B2
(45) Date of Patent: Nov. 16, 2010

(54) DEVICE AND METHOD FOR TREATING FOOT WITH ADUSTABLE BLADDER

(75) Inventors: Christopher P. Chiodo, Walpole, MA (US); Brent G. Parks, West Friendship, MD (US); Lew C. Schon, Baltimore, MD (US); Wu Zhang, Proctorville, OH (US); George Borak, Barboursville, WV (US)

(73) Assignee: Darco International, Inc., Huntington, WV (US)

( * ) Notice: Subject to any disclaimer, the term of this patent is extended or adjusted under 35 U.S.C. 154(b) by 274 days.

(21) Appl. No.: 11/689,578

(22) Filed: Mar. 22, 2007

(65) Prior Publication Data

US 2007/0260164 A1    Nov. 8, 2007

Related U.S. Application Data

(60) Provisional application No. 60/784,494, filed on Mar. 22, 2006.

(51) Int. Cl.
*A61F 5/00* (2006.01)
*A61F 5/37* (2006.01)
*A61H 7/00* (2006.01)

(52) U.S. Cl. .................. 602/27; 602/13; 128/882; 601/148; 601/151

(58) Field of Classification Search .............. 602/13, 602/27, 28, 29, 30, 36; 2/22, 24; 601/148, 601/149, 151, 152; 128/882, 892, 869, 846; 606/201, 202, 203

See application file for complete search history.

(56) References Cited

U.S. PATENT DOCUMENTS

| 5,453,082 | A  | * | 9/1995  | Lamont       | 602/27  |
|-----------|----|---|---------|--------------|---------|
| 5,584,798 | A  | * | 12/1996 | Fox          | 601/152 |
| 5,613,941 | A  | * | 3/1997  | Prengler     | 602/13  |
| 5,799,659 | A  |   | 9/1998  | Stano        |         |
| 5,887,591 | A  | * | 3/1999  | Powell et al.| 128/882 |
| 6,010,468 | A  | * | 1/2000  | Grove et al. | 601/23  |
| 6,592,534 | B1 | * | 7/2003  | Rutt et al.  | 601/151 |
| 6,669,660 | B2 |   | 12/2003 | Branch       |         |
| 7,056,299 | B2 |   | 6/2006  | Brown et al. |         |
| 7,063,727 | B2 | * | 6/2006  | Phillips et al.| 623/52 |
| 7,128,725 | B2 |   | 10/2006 | Rabe         |         |

* cited by examiner

*Primary Examiner*—Patricia M Bianco
*Assistant Examiner*—Ophelia Hawthorne
(74) *Attorney, Agent, or Firm*—Sughrue Mion, PLLC

(57) ABSTRACT

A device and method for treating a foot and ankle with a splint and an adjustable bladder. The method includes providing a device including a rigid splint that maintains a heel of the foot and at least one adjustable bladder provided underneath only a front of the foot; adjusting an inflation of the at least one bladder to a treatment inflation state; and maintaining a foot and ankle within the device for an extended period of time such that the foot and ankle are substantially immobilized in a dorsiflexion position or the foot and ankle are substantially immobilized in a position whereby plantarflexion is provided to the ankle.

27 Claims, 9 Drawing Sheets

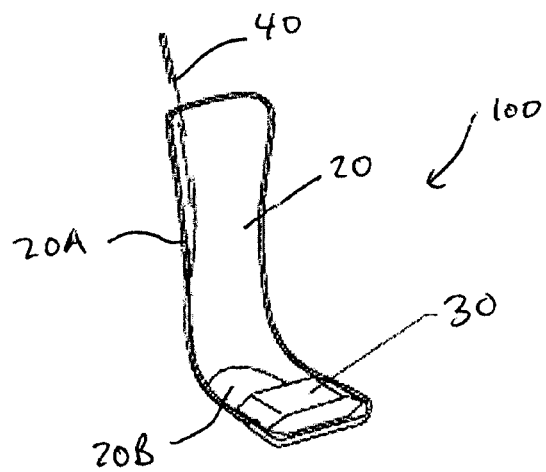
FIG. 1A
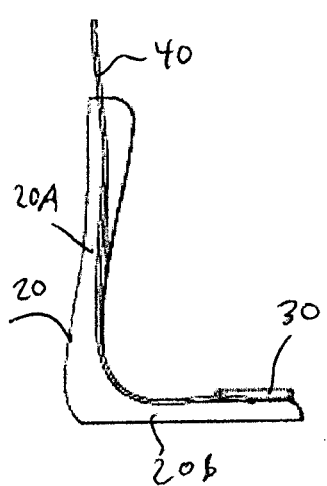 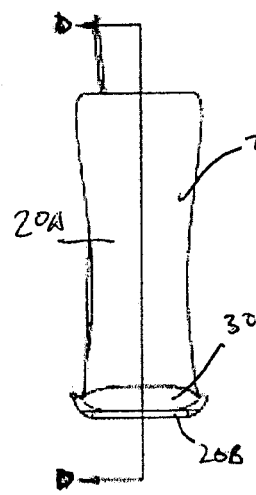 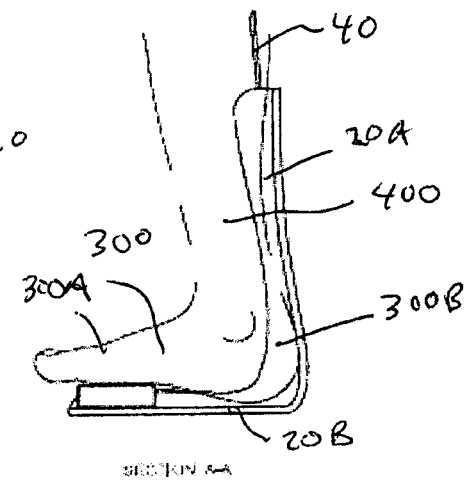
FIG. 1B  FIG. 1C  FIG. 1D

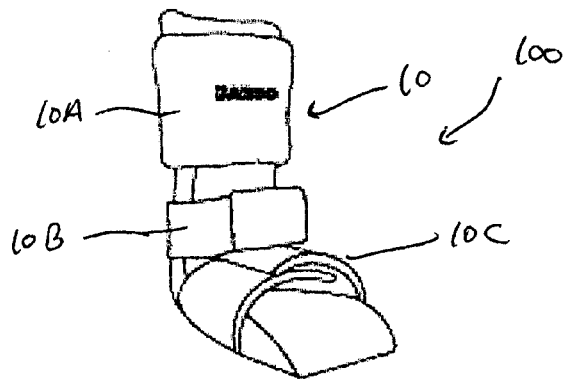
FIG. 2A
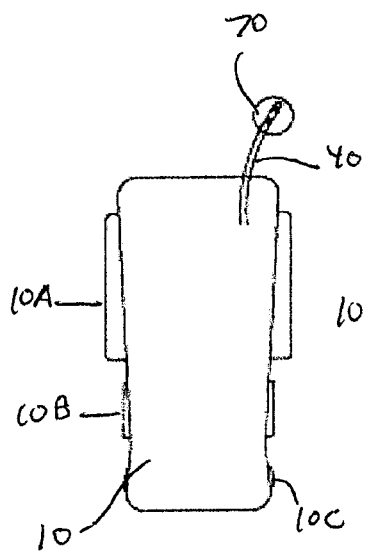 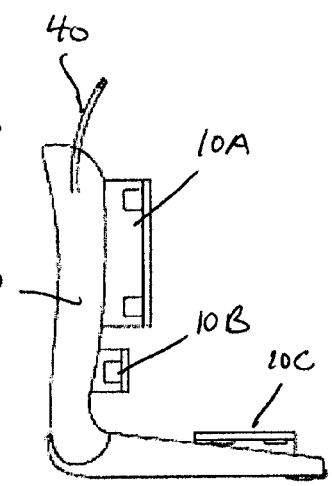 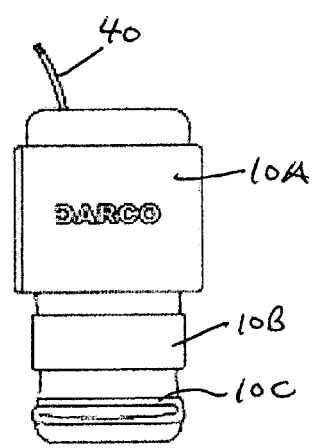
FIG. 2B  FIG. 2C  FIG. 2D

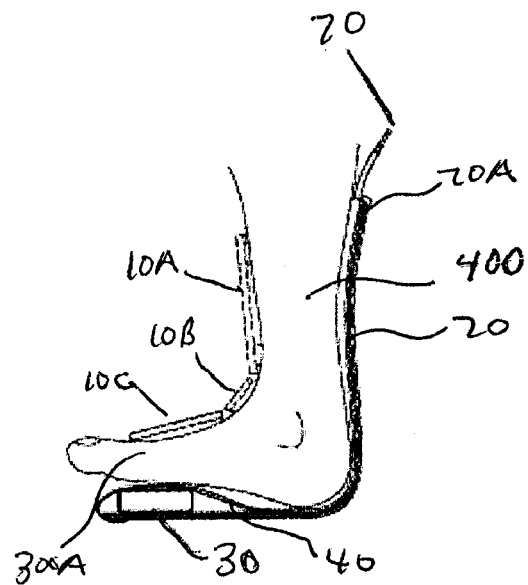
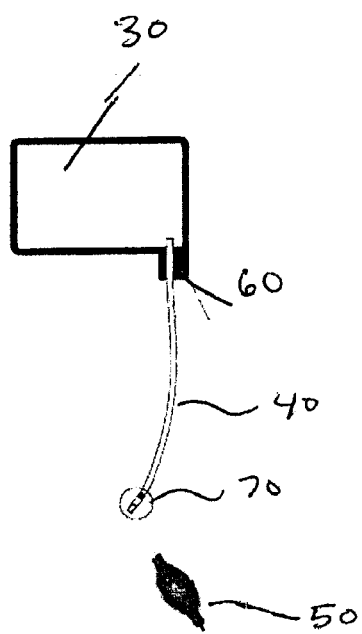
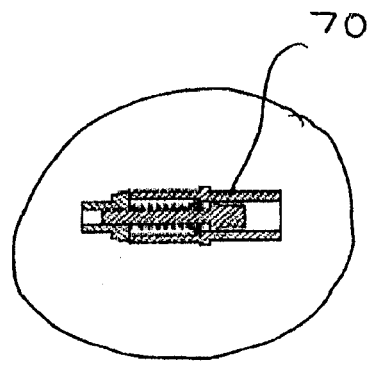
FIG. 3
FIG. 4A
FIG. 4B

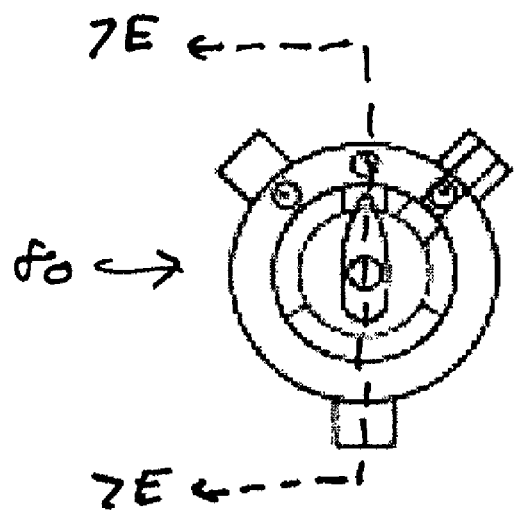 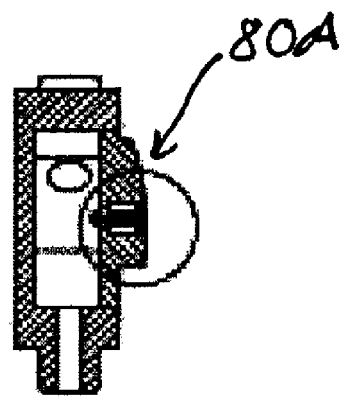
FIG. 7D      FIG. 7E
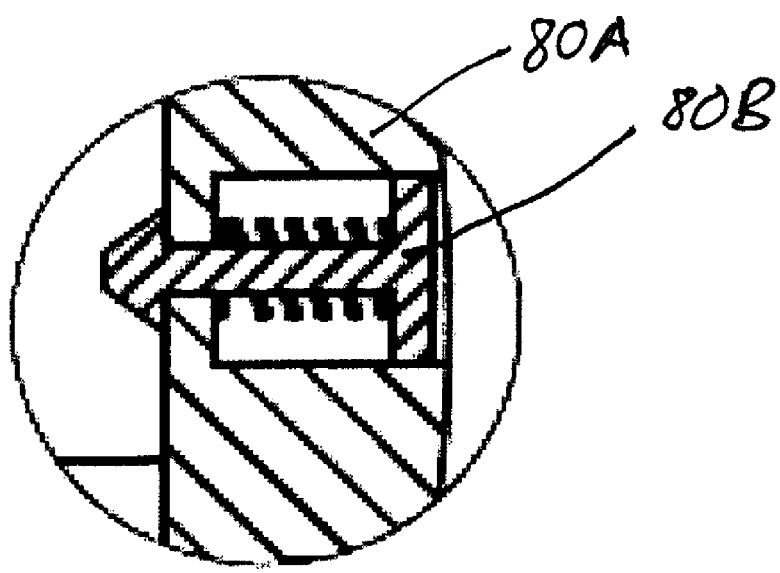
FIG. 7F

DEVICE AND METHOD FOR TREATING FOOT WITH ADUSTABLE BLADDER

CROSS-REFERENCE TO RELATED APPLICATIONS

This application claims priority under 35 U.S.C. §119(e) to U.S. Provisional Application No. 60/784,494, filed on Mar. 22, 2006, entitled "Air Night Splint Device," and incorporated herein by reference in its entirety.

BACKGROUND

1. Field of the Invention

Devices and methods consistent with this invention relate generally to treating a foot and ankle, and more particularly, to treating a foot and ankle using a splint and an adjustable bladder.

2. Description of the Related Art

The plantar fascia is a fibrous band of tissue that supports the arch of the foot. The plantar fascia extends from the bottom surface of the heel bone to the bottom of the feet just behind the toes. If the plantar fascia becomes stretched or strained, the arch and heel bone area of the foot can become tender and swollen. This is referred to as plantar fasciitis, a common and painful medical condition of the foot.

Often, plantar fasciitis is caused by the over-extension of the Achilles tendon, which extends upward from the heel in the back of the lower leg. That is, during physical activity and/or during sleep, a person's Achilles tendon can extend beyond a position that normally occurs when one stands, walks, runs, or sits. When the Achilles tendon extends in this way, the person's ankle tends to also have plantar flexion (i.e., flexion beyond 90 degrees), which stretches the plantar facia.

Patients have successfully treated plantar faciitis by wearing a rigid splint at night while sleeping. The splint includes an upper portion and a lower portion, and the lower portion extends at an angle of less than 90 degrees with respect to the upper portion. By wearing this splint, the patient's ankle is maintained in a state of dorsiflexion (i.e., flexion less than 90 degrees) and the planta facia is prevented from extending at night.

Prior devices for stretching and splinting the leg, ankle and foot apply pressure by way of solid or semi-rigid supports, often cushioned with fabric, foam or other solid or semi-solid materials. The amount of ankle dorsiflexion and stretching may be adjusted by way of strap(s), hinge(s), solid or foam wedge(s), or the shape of the device itself. Obtaining ankle dorsiflexion in such a manner may result in suboptimal contact and loading of the midfoot or forefoot. For instance the use of a wedge placed between the foot and splint could cause point loading of the metatarsal head(s). Such point loading could result in discomfort and reduced compliance, thereby compromising the efficacy of the device.

Stiffness and/or contracture of the gastrocnemius fascia, Achilles tendon, plantar fascia, and other soft tissues of the foot and ankle (heretofore known as "said anatomic structures") are associated with several pathologic conditions. These conditions include but are not limited to: plantar fasciitis, heel spurs, Achilles tendonitis, Achilles tendinosis, metatarsalgia, ankle contracture, painful callosities, and ulcerations. Accordingly, the treatment of these conditions may include the use of exercises, therapy and devices designed to splint and/or stretch the said anatomic structures. One device or class of devices is worn by the patient while at rest, usually at night, and therefore commonly referred to as a "night splint."

U.S. Pat. No. 5,799,659 issued to Stano, which is incorporated herein by reference, discloses a night splint that includes removable wedges provided within the splint. The removable wedges allow the angle of dorsiflexion to be adjusted by the patient. However, ability of the patient to vary the angle of dorsiflexion is limited by the number of removable wedges that are provided with the splint.

To splint and/or stretch the foot and ankle while at rest, a variety of devices have been developed. Despite the extensive development of such devices, they continue to exhibit certain disadvantages. For example, their designs are: (1) too complex, (2) too costly, (3) and may result in suboptimal contact and loading of the midfoot or forefoot. Thus, there exists a continuing need for the development of new and improved, easier to use and inexpensive devices for stretching and/or splinting said anatomic structures associated with said pathologic conditions. Accordingly, it would be beneficial to provide a splint that does not have multiple removable parts, which the patient may misplace. Moreover, it would be beneficial to provide a splint that provides the patient with the flexibility to adjust the angle of dorsiflexion to many different angles.

SUMMARY OF THE INVENTION

According to a first exemplary aspect of the invention, there is provided a method for treating a foot and ankle, including: providing a device, including a rigid splint that maintains a heel of the foot and at least one adjustable bladder provided underneath only a front of the foot; adjusting an inflation of the at least one bladder to a treatment inflation state; and maintaining a foot and ankle within the device for an extended period of time such that the foot and ankle are substantially immobilized in a position whereby dorsiflexion is provided to an ankle or the foot and ankle are substantially immobilized in a position whereby plantarflexion is provided to the ankle.

According to a second exemplary aspect of the invention, there is provided a device for treating a foot and ankle, including: a rigid splint that supports a heel portion of the foot; an adjustable bladder provided underneath only a front of the foot. The bladder is adjustable to a treatment inflation state whereby dorsiflexion is provided to an ankle, and the rigid splint includes an upper portion and a lower portion. The lower portion extends at an angle of less than 90 degrees with respect to the upper portion.

According to a third exemplary aspect of the invention, there is provided a device for treating a foot and ankle, including: a rigid splint that supports a heel portion of the foot; and a plurality of adjustable bladders provided side-by-side with respect to a width direction and provided underneath only a front of the foot. The bladders are adjustable to a treatment inflation state whereby dorsiflexion is provided to an ankle.

According to a fourth exemplary embodiment of the invention, there is provided device for treating a foot and ankle, including a rigid splint that supports a heel portion of the foot, the rigid splint including an upper portion, which supports a lower leg, and a lower portion, which supports the foot; and an adjustable bladder provided underneath only a rear of the foot. The bladder being adjustable to a treatment inflation state whereby plantarflexion is provided to an ankle.

BRIEF DESCRIPTION OF THE DRAWINGS

The nature and features of the invention will be more fully apparent upon consideration of the exemplary embodiments of the invention, which are schematically set forth in the drawings, in which:

FIGS. 1A-1D show the interior of a splint device for treating a foot in accordance with an exemplary embodiment of the present invention;

FIGS. 2A-2D show the exterior of the splint device shown in FIGS. 1A-1D;

FIG. 3 shows a patient's foot secured within the splint device shown in FIGS. 1A-1D;

FIG. 4A shows an adjustable bladder provided within a splint device and a tube for supplying air to the bladder;

FIG. 4B shows detail of a valve provided on the end of the tube shown in FIG. 4A;

FIGS. 7A-7E show details of the control valve;

DETAILED DESCRIPTION OF THE EXEMPLARY EMBODIMENTS

A splinting/stretching device is placed along the posterior leg, lower leg, ankle, and foot, and has a one or more dynamic adjustable pneumatic cell systems. These cell systems serve to both cushion the heel and dorsiflex the ankle, thereby stretching the gastrocnemius fascia, Achilles tendon, and plantar fascia. The purpose of said device and said stretching is to alleviate symptoms associated with such diseases as plantar fasciitis, heel spurs, Achilles tendonitis, Achilles tendinosis, metatarsalgia, ankle contracture, callosities, and ulcerations (collectively referred to as "pathologic conditions"). Furthermore, the device specifically addresses plantar foot and heel pain caused by conditions or anomalies of the plantar arch and heel venous plexus. A splint device in accordance with an exemplary embodiment of the present invention permits pneumatic compression of the venous plexus and may additionally provide intermittent pulsations to stimulate proper blood and extra cellular fluid flow.

Figure 11:
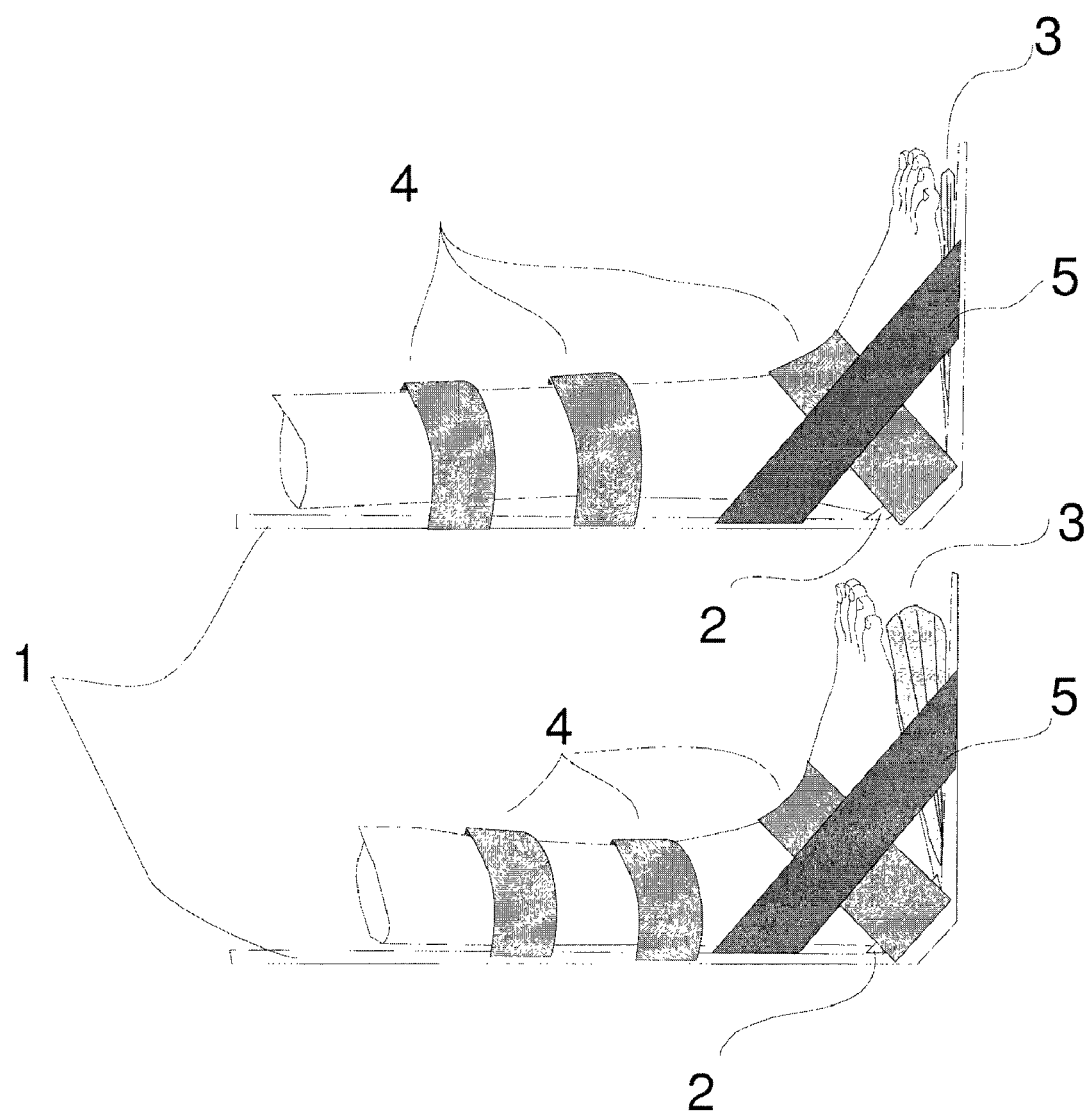
FIG. 11 shows a splint device in accordance with an exemplary embodiment of the present invention.

FIG. 11 shows a splint device in accordance with a first exemplary embodiment of the invention. The splint includes a rigid support brace 1, a heel support bladder 2, and an adjustable bladder 3, which is provided under the forefoot in FIG. 11. In the lower view in FIG. 11, the adjustable bladder 3 is filled to upwardly flex the forefoot of the patient. In the upper view in FIG. 11, the adjustable forefoot bladder 3 is mostly emptied to relax the forefoot of the patient. Securing straps 4 attach the splint to the lower leg and foot of the person. Support strap 5 provides additional rigidity to the support brace 1. Further, the support strap 5 provides the ability to perform gross adjustments to dorsi-plantar flexion.

The adjustable bladder 3 may alternatively be positioned under the midfoot (i.e. arch of the foot). In another exemplary embodiment, adjustable bladders may be positioned under both the midfoot and the forefoot. The adjustable bladder 3 serves to apply variable amount of pressure to the bottom of the forefoot and/or midfoot, thus resulting in a varying amount of ankle dorsiflexion and a varying amount of stretching of the gastrocnemius, Achilles tendon, and plantar fascia. The adjustable bladder 3 may be filled with air and may be adjusted by means of a compressible air chamber or bulb (not shown), secured (permanently or in other relatively secure manner) to the splint device. The adjustable bladder 3 may be inflated by compressing the air chamber. Excessive pressure within the adjustable bladder 3 may be released by opening a pressure release valve (not shown). The air chamber and release valve may be positioned so that the user does not have to disconnect or remove any part of the splinting/stretching device to perform the adjustments. In this way, the person's capacity to tolerate corrective stretching position is utilized fully. The person's ability to tolerate pressure is usually the limiting factor in a splinting/stretching system; therefore, it is the optimal utilization of that tolerance that helps optimize the whole system.

The adjustable bladder may be filled with a fluid other than air. Such alternative fluids can include, for example, water, gel, or other liquid. The adjustable bladder(s) may have a flat, convex, or concave surface where they contact the foot. The surface of the adjustable bladder(s) adjacent to the bottom of the foot may be soft or conformable enough to conform to the bottom of the foot.

The adjustable bladder may be connected to an air pump capable of providing intermittent pressure. The adjustable bladder is then pressurized and depressurized. The pump may be configured to provide pulsating pressure in the adjustable bladder. An additional pump and adjustable bladder may be provided to bladders along the calf to provide a venous pump to aid blood flow.

A second exemplary embodiment of the invention is shown in FIGS. 1-4A. The device 100 for treating a patient's foot 300 includes a rigid splint 20 that supports a heel portion 300B of the foot 300 and an adjustable bladder 30 that is provided underneath only a front 300A of the foot 300. The bladder 30 is adjustable to a treatment inflation state whereby dorsiflexion is provided to the patient's ankle.

FIGS. 1A-1D show an interior of the device 100. A rigid splint 20 is provided within a soft covering 10 (shown in FIGS. 2A-2D) and an adjustable bladder 30 is provided on the splint 20. The splint 20 can be made of a rigid material, such as polypropylene or plastic, but the invention is not limited in this respect.

FIG. 1A shows a three-dimensional view of the interior parts, while FIGS. 1B, 1C, and 1D, respectively, show a side view, a front view, and a D-D sectional view of the adjustable bladder 30 and splint 20.

As shown in these figures, the splint 20 includes an upper portion 20A and a lower portion 20B. The lower portion 20B, which supports the patient's foot 300, extends at an angle of less than 90 degrees with respect to the upper portion 20A, which supports the patient's lower leg 400. Both portions 20A, 20B of the splint 20 are substantially U-shaped so as to provide a shell for supporting the patient's foot 300, lower leg 400, and heel 300B.

As shown in FIG. 1D, the adjustable bladder 30 can be inflated to a treatment inflation state. At this state, patient's foot 300 is supported in a position whereby dorsiflexion is provided to the patient's ankle. The bladder 30 can be made of for example, polyurethane, but the invention is not limited in this respect. In order to provide the dorsiflexion, the bladder 30 is configured so that it is provided only underneath a front 300A of the patient's foot 300. As shown in FIG. 1A, the bladder 30 can have a substantially box shape with inclined side portions; however, the invention is not limited in this respect.

FIGS. 2A-2D show an exterior of the second exemplary embodiment of the device 100 for treating a foot 300. FIG. 2A is a three-dimensional view of the exterior of the device 100.

The rigid splint 20 (shown in FIGS. 1A-1D) is substantially surrounded by a soft covering 10, which can be made of cloth, or another soft material. The rigid splint 20 and adjustable bladder 30 can be enclosed within the soft covering 10. The adjustable bladder 30 can be fixed in position on the rigid split. Alternatively, the adjustable bladder can be removably connected to the rigid splint 20 by hook-and-loop fasteners (i.e., VELCRO connection) or by being enclosed within a groove or pocket (not shown) within the soft covering 10.

The device 100 also includes some structure for securing the patient's foot 300 for an extended period of time so that the foot 300 is substantially immobilized in a position whereby dorsiflexion is provided the patient's ankle. In this exemplary embodiment, the structure for securing the foot is several sets of straps 10A, 10B, 10C, that are connected by hook-and-loop fasteners. However, the invention is not limited in this respect, and some other conventional structure for connecting straps, such as a button, a lace, tie, or a zipper may be used.

In this exemplary embodiment, three sets of straps 10A, 10B, and 10C, which can also be made of cloth, are provided. The strap 10A secures the device 100 to an upper part of a patient's lower leg 400, the strap 10B secures the device 100 to a lower part of the patient's lower leg 400, and the strap 10C secures the device to the patient's foot 300. FIGS. 2B, 2C, and 2D, respectively, show a rear view, side view, and front view of the device 100 including the straps 10A, 10B, 10C.

FIG. 3 shows the patient's foot 300 secured within the device 100. The straps 10A, 10B, and 10C maintain the patient's foot 300 within the device 100 such that the foot 300 is substantially immobilized in a position whereby dorsiflexion is provided to the patient's ankle. Thus, when a patient wears the device for an extended period of time, such as during sleeping, the patient's foot can be treated for plantar faciitis or other foot and ankle problems.

FIG. 4A shows a tube 40 that is sealed to the bladder 30, for example by ultrasonic or heat welding 60. The tube 40 supplies air (i.e., a fluid) to the adjustable bladder 30. The tube includes a valve 40 that is connectable to a hand pump 50. Details of the valve 70 are shown in FIG. 4B.

By connecting the hand pump 50 to the valve 70, the patient can provide air to the bladder 30. By controlling the amount of air pumped into the bladder 30, the patient can adjust the inflation state, or height, of the bladder 30 until the bladder 30 is provided at a desired treatment inflation state whereby the proper amount of dorsiflexion is provided to the patient's ankle. Moreover, the patient can release excess air from the bladder 30 by opening the valve 70.

As shown in FIG. 3, the valve 70 can be provided near a top 20A of the splint 20, and the tube 40 can extend downward from a top 20A of the rigid splint 20 at a position behind the splint 20. This position allows the patient to adjust the amount of dorsiflexion while the patient's foot 300 is provided within the device 100.

Accordingly, a patient's foot 300 may be treated by providing the device 100, adjusting an inflation of the bladder 30 to a desired treatment inflation state, and maintaining a foot 300 within the device 100 for an extended period of time such that the foot 300 is substantially immobilized in a position whereby dorsiflexion is provided to the ankle. This can be accomplished, for example, when the patient is sleeping.

Figure 5:
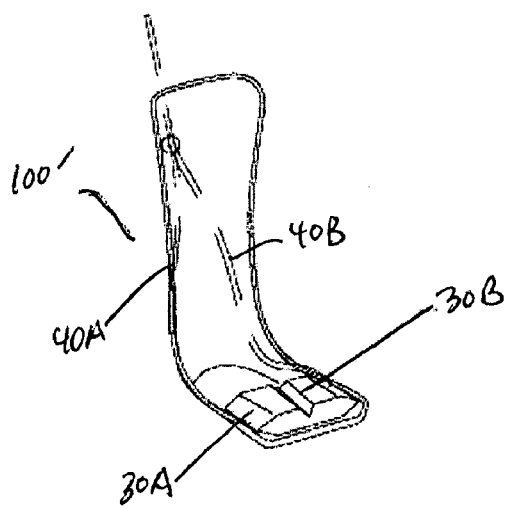
FIG. 5 shows a splint device in accordance with an exemplary embodiment of the present invention.

A third exemplary embodiment of the invention is shown in FIGS. 5-7C. As shown in FIG. 5, this exemplary embodiment is essentially the same as the second exemplary embodiment except that, instead of a single adjustable bladder 30, two bladders 30A, 30B are provided side-by side with respect to a width direction of the device 100'. This exemplary embodiment includes two tubes 40A, 40B that independently provide air to the two bladders 30A, 30B, respectively. Like the second exemplary embodiment, the bladders 30A, 30B can be made of for example, polyurethane, and the tubes 40A; 40B can be sealed to the bladder 30 by, for example, ultrasonic or heat welding.

Sometimes it is desirable for a patient's foot and ankle to be immobilized in a position of inversion (i.e., movement of the sole of the foot toward the midline of the body) or eversion (i.e., movement of the sole of the foot away from the midline of the body). By using two bladders 30A, 30B, the patient can independently adjust the desired treatment inflation state of each bladder 30A, 30B and, therefore, provide the foot 300 in a position of inversion or eversion.

Figure 6:
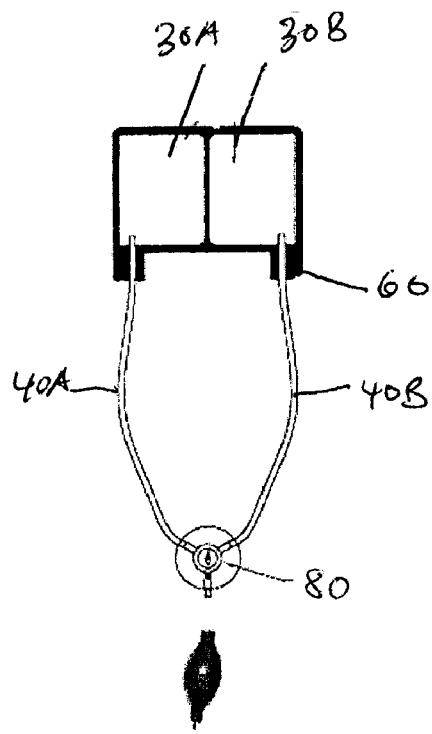
FIG. 6 shows the adjustable bladders and control valve of the splint device shown in FIG. 5.
Figures 7A, 7B, 7C:
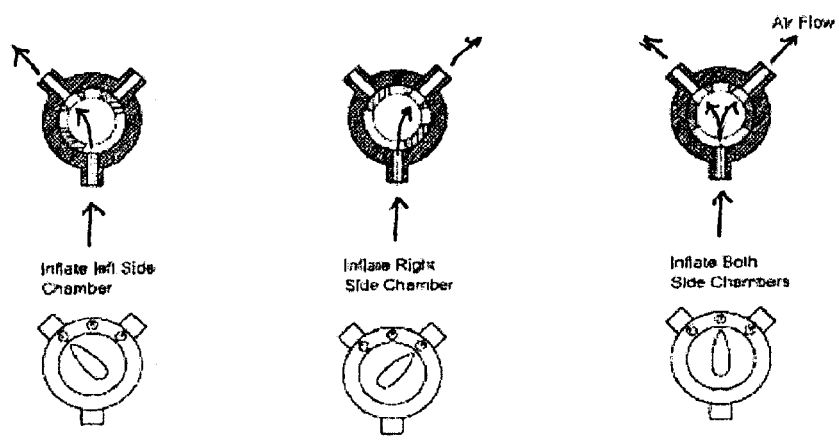

As shown in FIG. 6, the device 100' includes a control valve 80, which controls whether air is pumped to the bladder 30A, to the bladder 30B, or both bladders 30A, 30B. This control valve 80 is shown in detail in FIGS. 7A-7C with the top part of each figure showing an interior of the control valve 80, and the bottom part of each figure showing an exterior of the control valve 80. FIG. 7A shows a control 80A of the control valve 80 positioned so that air is only supplied to the left bladder 30A, FIG. 7B shows the control 80A of the control valve 80 positioned so that air is only supplied to the right bladder 30B, and FIG. 7C shows the control 80A of the control valve 80 positioned so that air is supplied to both bladders 30A, 30B.

Moreover, as shown in FIGS. 7D-7F, the patient can release excess air from the bladders 30A, 30B by opening a valve release 80B that is provided within the control 80A of the valve 80. FIG. 7D shows a front of the control valve 80, FIG. 7E shows a 7E-7E cross sectional view of the control valve 80, and FIG. 7F shows a partial enlarged view of the control 80B of the control valve 80. When the control 80A is in the position of FIG. 7A, air can be evacuated from the left bladder 30A by pressing the spring-biased valve release 80B. Likewise, air can be evacuated from the right bladder 30B by pressing the spring-biased valve release 80B when the control 80A is in the position of FIG. 7B, and air can be evacuated from both bladders 30A, 30B when the control valve 80A is in the position of FIG. 7C.

Figure 8A:
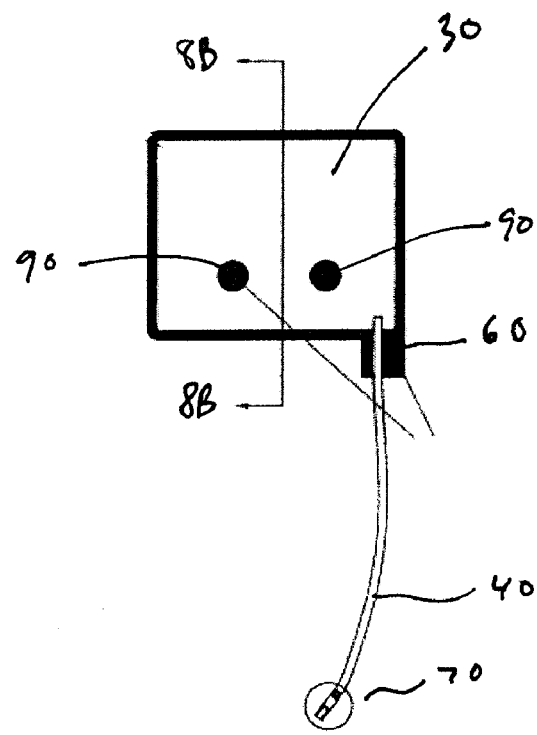
FIGS. 8A and 8B show a modification of the splint device shown in FIGS. 1A-1D in which the bladder includes weld spots.
Figure 8B:
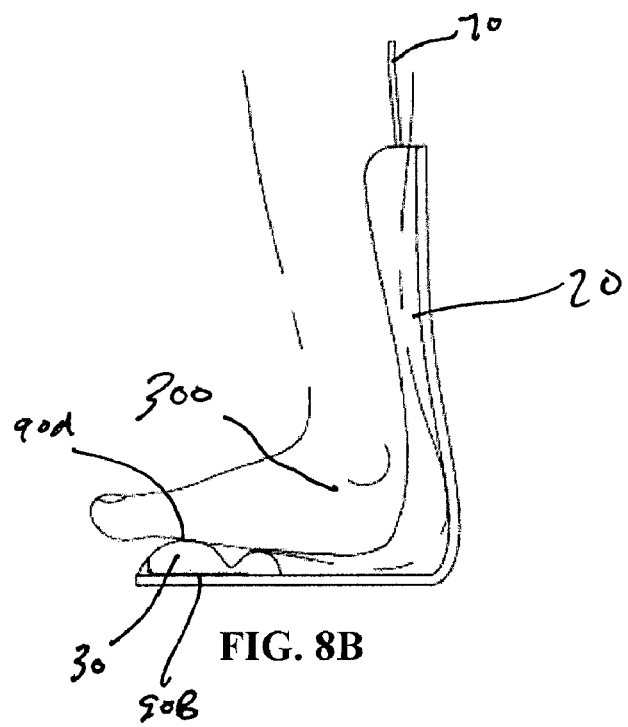

FIGS. 8A and 8B show a modification of the second exemplary embodiment. In this modification, the bladder 30 includes weld spots 90 that connect portions of upper and lower walls 90A, 90B of the bladder together. The weld spots 90 may be provided, for example, by ultrasonic or heat welding. The weld spots 90 allow the inflated bladder 30 to have a tapered angle that is more comfortable for the patient's foot 300. FIG. 8A is a view of the bladder 30 with two weld spots, and FIG. 8B shows an 8B-8B cross-sectional view of the resulting bladder 30, which has a shape that is comfortable for the patient's foot 300 in the position where the foot and ankle ares substantially immobilized in a position whereby dorsiflexion is provided to an ankle.

Figure 9:
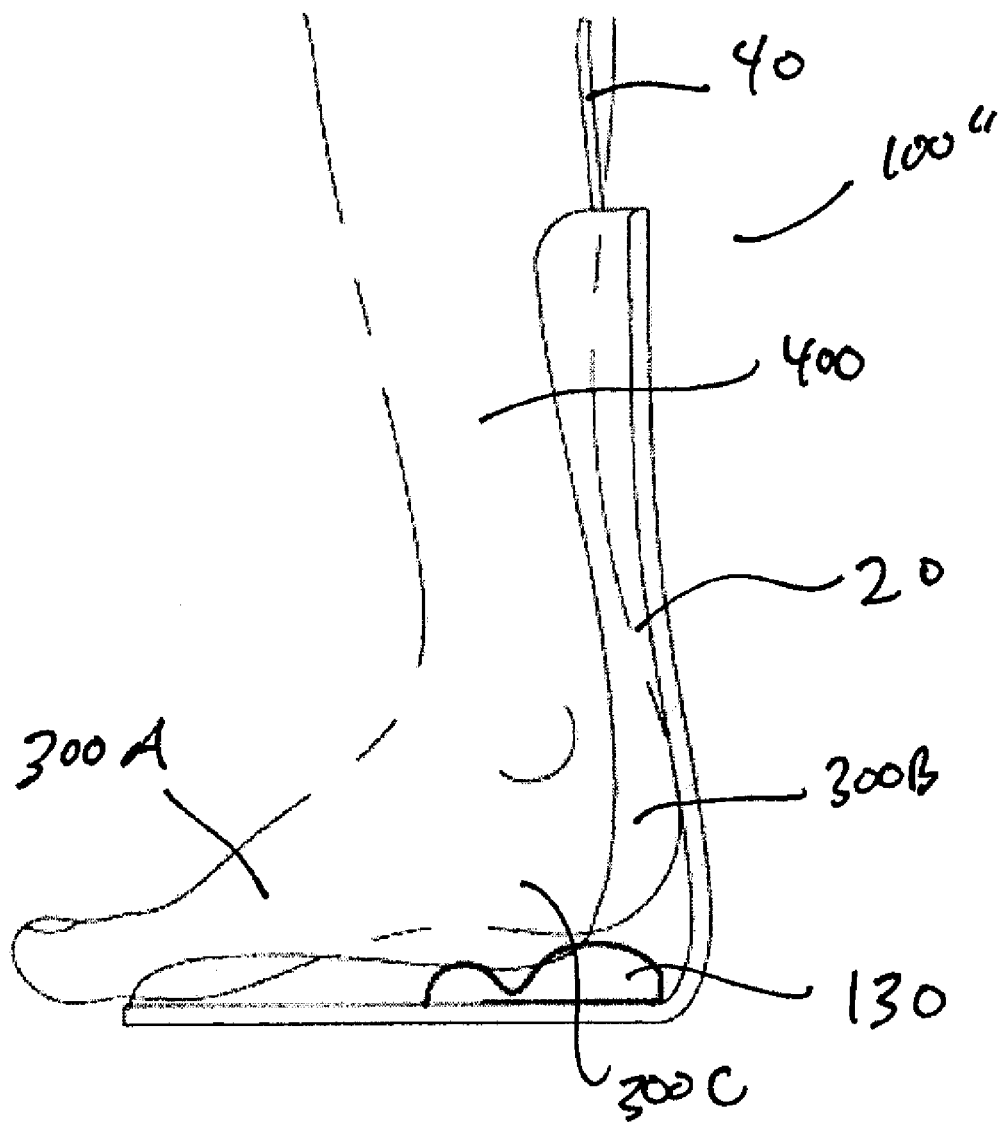
FIG. 9 shows a splint device in accordance with an exemplary embodiment of the present invention.

Finally, FIG. 9 shows a fourth exemplary embodiment of a device 100' for treating a patient's foot 300 in which a bladder 130, which is substantially the same as the bladder 30 discussed above with respect to the device 100 in FIGS. 1A-1D, is provided underneath only a rear 300C of the patient's foot 300. For example, as is shown in FIG. 9 the bladder 130 can be sealed to a tube 40 and can be shaped by weld spots 90. However, in contrast to the dorsiflexion position of the device 100, the second device positions the patient's foot 300 such that the foot and ankle 300 are substantially immobilized in a position whereby plantarflexion is provided to an ankle 300B.

If the adjustable bladder 30 is removably connected to the rigid splint 20, for example, by hook-and-loop fasteners or by being enclosed within a groove or pocket (not shown) within the soft covering 10, the device 100 can be easily converted into the device 100" by simply detaching the bladder 30 from the split 20 and reattaching the bladder 30 under a rear 300C of the foot 300.

Figure 10A:
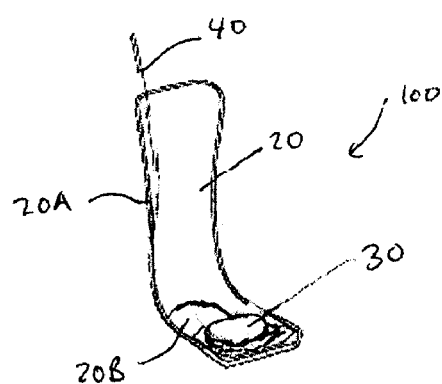
FIGS. 10A-10C are examples of different shapes that the bladder of the exemplary embodiments can take.
Figure 10B:
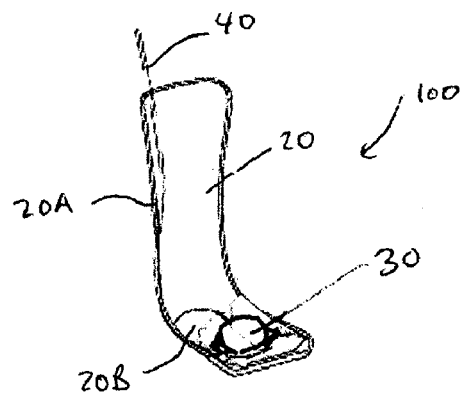
Figure 10C:
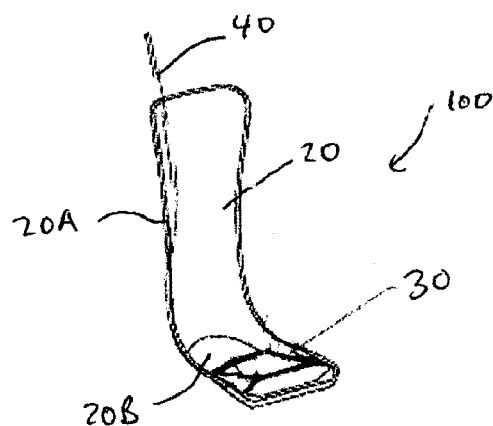

Finally, while the exemplary embodiments discussed above, for example, FIG. 1, show the bladder 30 having a substantially box shape with inclined side portions, the invention is not limited in this respect and the bladder 30 can have other shapes. For example, as respectively shown in FIGS. 10A, 10B, and 10C, the bladder 30 can have a substantially oval, substantially circular, or substantially inclined shape.

The invention is not limited to the exemplary embodiments described above. That is, departures can be made from the exemplary embodiment without departing from the spirit and scope of the invention, which is only limited by the following claims.

What is claimed is:

1. A method for treating a foot and ankle, comprising:
   providing a device, comprising a rigid splint that maintains a heel of the foot and at least one adjustable bladder provided either underneath only a front of the foot or underneath only a rear of the foot, wherein the rigid splint is comprised of only one piece; adjusting an inflation of the at least one bladder to a treatment inflation state; and maintaining a foot within the device for an extended period of time such that the foot is substantially immobilized in a position whereby dorsiflexion is provided and maintained to an ankle overnight if the at least one adjustable bladder is provided underneath only a front of the foot or the foot is substantially immobilized in a position whereby plantarflexion is provided and maintained to the ankle overnight if the at least one adjustable bladder is provided underneath only a rear of the foot, wherein the at least one adjustable bladder has a valve through which the at least one adjustable bladder can be inflated.

2. The method of claim 1, wherein the at least one bladder comprises first and second bladders provided side-by side with respect to a width direction of the device;
   wherein the width direction of the device corresponds to a width direction of a foot that the device is designed to accommodate.

3. The method of claim 2, further comprising supplying a fluid to the first bladder and the second bladder via first and second tubes, respectively.

4. The method of claim 3, further comprising controlling the supplying of the fluid to the first bladder and the second bladder via a control valve.

5. The method of claim 4, wherein the adjusting of the inflation of the at least one bladder to the treatment inflation state comprises attaching a pump to the valve and inflating at least one of the bladders.

6. The method of claim 2, further comprising adjusting an inflation of the first bladder and/or the second bladder in order to provide inversion or eversion of the foot and ankle.

7. The method of claim 1, wherein the foot and ankle are substantially immobilized in a position whereby dorsiflexion is provided to an ankle.

8. The method of claim 7, wherein the rigid splint has a substantially L-shape and comprises an upper portion, which supports a lower leg and a lower portion, which supports the foot.

9. The method of claim 8, wherein the device further comprises a soft covering that substantially surrounds the rigid splint, wherein the bladder is secured within the soft covering.

10. The method of claim 9, wherein the upper portion and lower portion are both substantially U-shaped members.

11. The method of claim 1, further comprising supplying a fluid to the at least one adjustable bladder via at least one tube.

12. The method of claim 11, wherein the adjusting of the inflation of the at least one bladder to the treatment inflation state comprises attaching a pump to a valve and inflating the bladder.

13. The method of claim 1, wherein the foot is substantially immobilized in a position whereby plantarflexion is provided to an ankle.

14. The method of claim 13, wherein the device further comprises a soft covering that substantially surrounds the rigid split, wherein the bladder is secured within the soft covering.

15. The method of claim 1, wherein the at least one adjustable bladder is removably connected to the rigid splint so that the at least one adjustable bladder can be provided both underneath only a front of the foot and, at a different time, underneath only a rear of the foot.

16. A device for treating a foot and ankle, comprising:
    a rigid splint that supports a heel portion of the foot, the rigid splint having a substantially L-shape and comprising an upper portion, which supports a lower leg, and a lower portion, which supports the foot and ankle;
    at least one adjustable bladder provided underneath only a front of the foot, the at least one bladder being adjustable to a treatment inflation state whereby dorsiflexion is provided to an ankle;
    wherein the at least one adjustable bladder is the only structure capable of adjusting a flexion of the foot and ankle,
    wherein a rigid plate is not provided between the foot and the at least one adjustable bladder, and
    wherein the at least one adjustable bladder has a valve through which the at least one adjustable bladder can be inflated.

17. The device of claim 16, wherein the at least one bladder comprises first and second bladders provided side-by side with respect to a width direction of the device;
    wherein the width direction of the device corresponds to a width direction of a foot that the device is designed to accommodate.

18. The device of claim 17, further comprising two tubes, a first tube that supplies a fluid to the first bladder and a second tube that supplies the fluid to the second bladder.

19. The device of claim 18, further comprising a control valve that controls whether fluid is provided to the first bladder and second bladder.

20. The device of claim 16, further comprising a soft covering that substantially surrounds the rigid splint, wherein the bladder is secured within the soft covering.

21. The device of claim 20, wherein the upper portion and lower portion are both substantially U-shaped members.

22. The device of claim 16, further comprising a means for securing the foot for an extended period of time such that the foot and ankle are substantially immobilized in a dorsiflexion position.

23. The device of claim 16, further comprising a tube that supplies a fluid to the at least one adjustable bladder.

24. The device of claim 16, wherein the bladder comprises at least one weld spot that connects portions of upper and lower walls of the bladder together.

25. The device of claim 16, wherein the bladder is a substantially box shape, a substantially oval shape, a substantially circular shape, or a substantially inclined shape.

26. The device of claim 16, further comprising:
a tube that supplies a fluid to the at least one adjustable bladder, wherein an end portion of the tube is located near a top of the upper portion of the rigid splint.

27. The device of claim 16, wherein the foot comes in direct contact with the at least one adjustable bladder or the foot and the at least one adjustable bladder are only separated by a soft covering such that the at least one adjustable bladder accommodates the shape of the foot.

* * * * *